United States Patent [19]

Lazorthes

[11] Patent Number: 4,710,167

[45] Date of Patent: Dec. 1, 1987

[54] IMPLANTABLE DEVICE FOR CHRONICALLY INJECTING A SUBSTANCE, IN PARTICULAR A THERAPEUTANT

[75] Inventor: Guy Lazorthes, Toulouse, France

[73] Assignee: Applied Precision Limited, London, England

[21] Appl. No.: 865,412

[22] Filed: May 21, 1986

[30] Foreign Application Priority Data

May 21, 1985 [FR] France ............................ 85 08067

[51] Int. Cl.⁴ .............................................. A61M 5/00
[52] U.S. Cl. .................................... 604/93; 604/175; 604/891
[58] Field of Search ...................... 604/8-10, 604/93, 175, 185, 246, 212, 891

[56] References Cited

U.S. PATENT DOCUMENTS 3,310,051  3/1967  Schulte .......................... 604/212 X
4,405,305  9/1983  Stephen et al. ...................... 604/175
4,543,088  9/1985  Bootman et al. .................... 604/175
4,544,371  10/1985  Dormandy et al. ................. 604/891

FOREIGN PATENT DOCUMENTS 661236  11/1951  United Kingdom ................ 604/212

Primary Examiner—Dalton L. Truluck
Attorney, Agent, or Firm—Harold H. Dutton, Jr.

[57] ABSTRACT

The invention concerns a device to be implanted in an accessible subcutaneous zone of the body of a patient in order to constitute a chronic injection site of a liquid, in particular a therapeutant. This device includes an injection chamber (12) bounded by an integral rigid case (11) provided for that purpose with a recess of rounded, concave shape; the case (11) is provided around the recess with a rim (13) on which is impermeably fixed the rim of an elastic membrane (14) which in its rest state is essentially plane. A catheter (17) is connected to the injection chamber (12) and issues into the deepest part of the recess forming this chamber.

9 Claims, 11 Drawing Figures

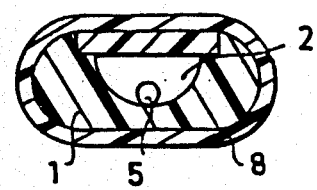
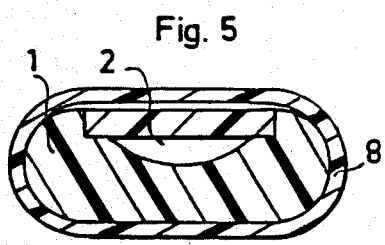
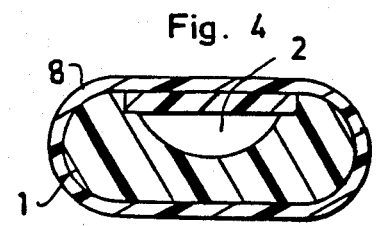
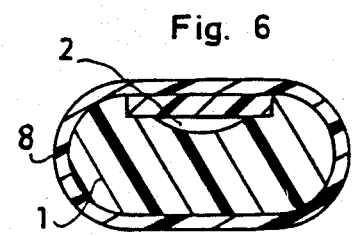
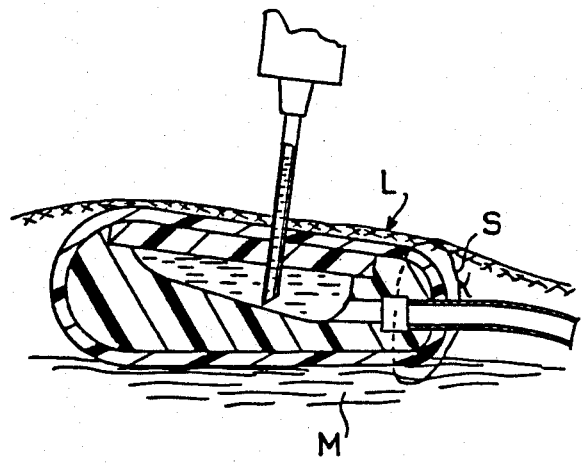

IMPLANTABLE DEVICE FOR CHRONICALLY INJECTING A SUBSTANCE, IN PARTICULAR A THERAPEUTANT

The invention concerns a device for total implantation in an accessible subcutaneous zone of a patient's body representing a chronic injection site for a liquid (and essentially therapeutic) substance.

BACKGROUND AND OBJECTS OF THE INVENTION

The recent technique of implantation sites comprises a local anesthesia procedures wherein an injection chamber is placed below the subcutaneous tissue in such a manner that this chamber is accessible through the skin; this chamber is connected to a catheter which feeds the substance directly to the applicable area of the body. These injection sites may remain over a long time within the body of the patient and make it possible to eliminate repeated intravenous, intra-arterial, intrarachidic, cerebral intraventricular or intraperitoneal injections and to replace them by simple subcutaneous injections.

A first type and presently commercially available device injects each time one dose of therapeutant (hereafter denoted by "embolus"). These devices include a rigid disk, especially one made of stainless steel over which there is an elastic silicone membrane acting as a deforming cone; the injection chamber a volume inside of this dome and communicates with a catheter. During the implantation, the dome is directed toward the skin line so as to be accessible on one hand to an injection needle and on the other hand manually through the skin.

Following implantation, this type of device is made operative by passing a needle mounted on a syringe through the membrane in order to feed the therapeutant to the inside of the deforming dome constituting the chamber (the metal disk sealing the chamber acting as a stop against the tip of the needle), and thereupon, after the needle has been withdrawn, the elastic dome is manually pressed through the skin in order to expel the therapeutant dose toward the catheter.

However devices of that kind incur several drawbacks. In the first place, they only allow injecting emboli by units and are inappropriate for long-term perfusions. This is so because the elastic dome of the device is unfit to keep stably in place a perfusion needle. Further, these devices have a relatively short service life because after several hundred injections, the elastic dome becomes the seat of micro-infiltrations: thereupon the device must be changed, and surgical intervention again is required. Also, such devices suffer from the major drawback that the embolus in the injection chamber formed by the deforming dome is never wholly expelled into the catheter when the operator manually presses on the dome no matter how much care is being expended; the variable slight amount of residual therapeutant in the dome after the pressure was exerted degrades the accuracy of the injected dose and in some treatments that may be highly prejudicial, especially when administering such active ingredients as opiates neuro-mediators, antimitotics, which require accurate dosage.

Another type of known device makes possible perfusion but lacks any manually actuated membranes for injecting emboli. These latter devices comprise a cylindrical chamber made of stainless steel which is closed on one side by a stainless steel bottom and on the other by a septum allowing to impermeably pass the perfusion needle. The essential drawback of these devices is that their usefulness is restricted to perfusion because they do not allow unit-feeding emboli corresponding to an accurate and predetermined amount of therapeutant; now there is presently such a need in very many therapeutic treatments (long-term chemotherapy, pain treatment by epidural or intrathecal morphine injections . . . ). Furthermore, the geometry of these devices requires a perpendicular puncture whereby practical difficulties are encountered to keep the needle in place during perfusion and in connecting it to the external supply system. Moreover, these devices also suffer from the disadvantage that they are fairly expensive and that their bulk is substantially larger than the flexible-dome devices (especially in height), whereby implantation is more difficult and causes a boss underneath the skin that might bother the patient.

The object of the present invention is to provide an improved device allowing universal application both for embolus injections and for extended perfusions.

Another main object of the invention is to provide a device capable of supplying an exact and predetermined dose of therapeutant in an injection.

Another object of the invention is to provide a device of much longer service life than the elastic-dome devices.

Another object is to provide an economical and compact device lending itself to easy implantation in the subcutaneous zone.

Another object is to provide a device entailing no risk at all of artifacts or interferences in exploration by modern imaging means (tomodensitometry, magnetic resonance . . . ).

DESCRIPTION OF THE INVENTION

To that end the device object of the invention and intended to constitute a chronic injection site of a liquid either in the form of dosed emboli or in perfused form comprises ;

- an injection chamber acting as a reservoir of liquid,
- and elastic membrane fitted to allow on one hand filling the chamber through said membrane and on the other hand expulsion of the liquid through pressure exerted on the membrane,
- and a catheter connected to the injection chamber.

In the present invention, this device is characterized in that:

- the injection chamber is bounded by an integral rigid case with a rounded, concave recess fashioned in its thickness,
- said recess is open on one side of said case and its depth is slight compared to the dimensions of its cross-sectional open side on the active side,
- the cross-section of said recess in sections parallel to the active side decreases as these sections approach the recess bottom,
- the case is provided with a duct issuing in the bottom of the recess and the catheter end is hermetically fixed in said duct,
- the case is provided around the recess with a peripheral rim on which the periphery of the elastic membrane is impermeably fastened,
- said elastic membrane is substantially plane in the rest position.

The position mentioned recess defines the capacity of the injection chamber and preferably has a volume between 0.2 and 1.7 cm³ for the present basic models so that the capacity of the chamber in the rest condition of the membrane corresponds to a unit dose of therapeutant (the magnitude of which as a rule will be within this range of values).

Two illustrative recesses are shown below; preferably their characteristic shapes are defined so as to correspond to the pressing forefinger, as a result of which the membrane shall inherently hug the bottom of the recess when forced back by the operator's forefinger.

The case of the device may be molded integrally from a biocompatible rigid plastic such as reinforced silicone or polycarbonate. This case essentially meets three functions:

in the first place it defines an injection-chamber shape allowing complete expulsion of the contained substance thanks to the ease of compressing the membrane against all of the recess surface of said body, also, it acts as a support by its peripheral rim to the periphery of the plane membrane fastened for instance by bonding to said rim, lastly, it acts as a limit stop for the injection or perfusion needle when the injection chamber is being filled.

The elastic membrane is cut to conform to the shape of the case's rim and is made of an elastic biocompatible plastic of the self-sealing type, in particular silicone. The plane shape of this membrane improves its impermeability after a great number of injections, as discussed further below. Also, this plane shape combined with the arrangement of the membrane on the case and the shape of the body's recess result in the following:

a natural capability of the membrane to deform and to hug the recess bottom of the case when manually compressed, an improvement of the stability of the perfusion needle whereby this type of injection can be performed without risk.

Accordingly the device of the invention combines the following properties: universal application as regards both embolus injections and perfusion injections, accuracy of injected dosage, extended service life because of better tightness following many perforations, economy because of simple geometry and ease of molding the body, and a relative device thinness facilitating its implantation.

In another feature of the invention, the case and the elastic membrane are wholly covered by a flexible coat made of a biocompatible material, in particular silicone. This coating increases the impermeability of the membrane following a large number of perforations and improves the biocompatibility of the device.

DESCRIPTION OF DRAWINGS

Further features, purposes and advantages of the invention will become clear in relation to the following description and to the attached drawings showing two preferred embodiments:

FIGS. 3, 4, 5 and 6 are cross-sections respectively through planes BB', CC', DD' and EE', FIGS. 7a, 7b and 7c illustratively show how to operate the device.

DESCRIPTION OF PREFERRED EMBODIMENTS

Figure 1:
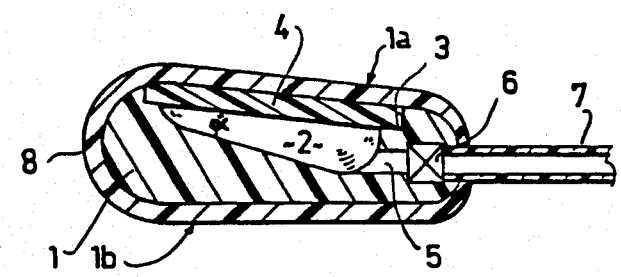
FIG. 1 is a section through a first embodiment mode along a longitudinal plane with an axis of symmetry AA'.
Figure 2:
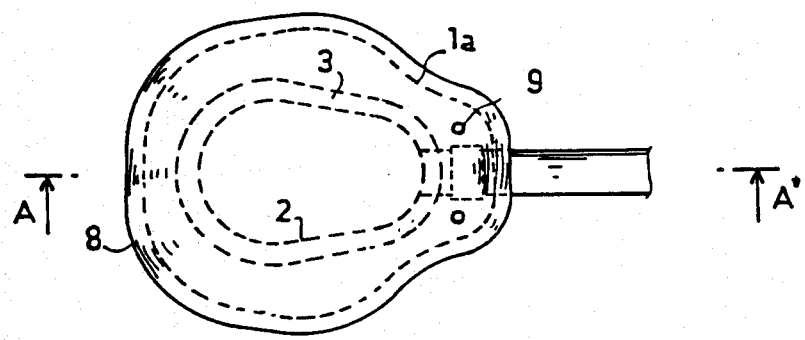
FIG. 2 is a topview.

The device is shown on scale actual size in FIGS. 1 through 7 and is intended to be a chronic-injection site of a substance into a specified region of the patient's body.

This device includes an integrally molded, rigid case 1 and of polycarbonate or silicone reinforced with dacron or polyetherisulfone; this case has a thickness which is about 10 mm less than its other dimensions. Seen in topview, it is elongated with a taper on one side (the right side in FIG. 2): its peripheral rim is rounded everywhere.

The upper side 1a of the case is called the active side and is slightly sloping with respect to the opposite side 1b, whereby the case's thickness decreases in the direction of the taper.

On its active side 1a, the case 1 has a recess 2 which is shallow with respect to the dimensions of its open cross-section at the active surface.

The depth of this recess increases toward its deeper portion near the tapered side of the case the shape of this recess matches that of a forefinger: it has a symmetrical elongation with respect to the longitudinal plane AA' and slightly narrows on the body's tapered side. Also, as shown in the Figures, the cross-section of the recess 2 in sectional planes parallel to its active side evinces a decreasing area as these planes approach the bottom of the recess.

In this example, the central portion of the recess bottom assumes a conical surface and extends on each side by rounded surfaces as far as the opening cross-section on the active side; this bottom slopes longitudinally toward the deepest part so as to subtend in the plane of symmetry AA' an angle alpha with the active side 1a which is approximately between 10° and 15°.

Around the recess 2, the case comprises a plane rim 3 onto which is tightly bonded the periphery of an elastic silicone membrane 4 of the self-sealing type which closes the recess; this membrane may be of the silicone-plug type.

This membrane 4 when at rest is planar and slants like the active side of the case; it is cut out in such a manner as to hug the shape of the rim 3; it may deform to hug the bottom of the recess over its entire surface.

In this example the volume of the recess 2 is about 1.3 to 1.6 cm³ (for instance 1.5 cm³) and thereby bounds an injection chamber of which the maximum capacity equals this volume and may be reduced to an essentially null value by compressing the membrane 4.

The case 1 in mid-thickness has a duct 5 in the plane of symmetry between the active surface 1a and the opposite surface 1b nearly parallel to the latter. On one side this duct issues into the recess 2 where it is deepest, and on the other side this duct has a larger diameter issuing to the outside of the case.

A known antibacterial filter 6 (in particular a microporous filter) is located in the wider section of the duct 5 and rests against the shoulder defined by the change in diameter.

The end of a flexible catheter 7 is fastened by bonding to said duct near the filter 6 (which is located immediately upstream of this end). This catheter 7 issues from the case in a longitudinal direction approximately parallel to the plane of the side 1b.

The case 1 and the membrane 4 are entirely covered with a flexible silicone coat 8. This coat is put in place after bonding the membrane and the catheter in any known manner, for instance by molding, dipping, spraying . . .

Suture apertures such as 9 passing through the thickness of the device also pass on either side of the catheter 7 through the case and the coat.

Figure 7B:
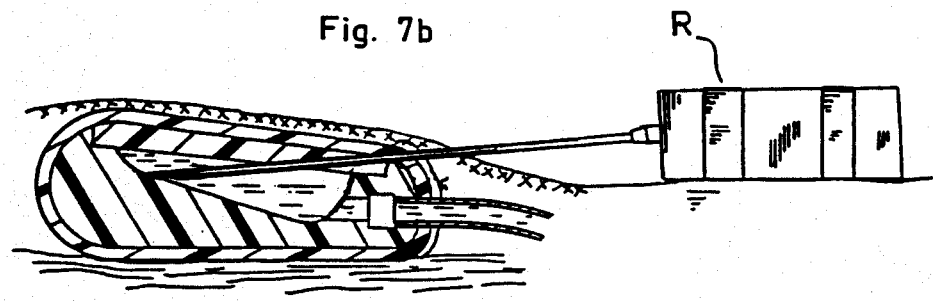
Figure 7C:
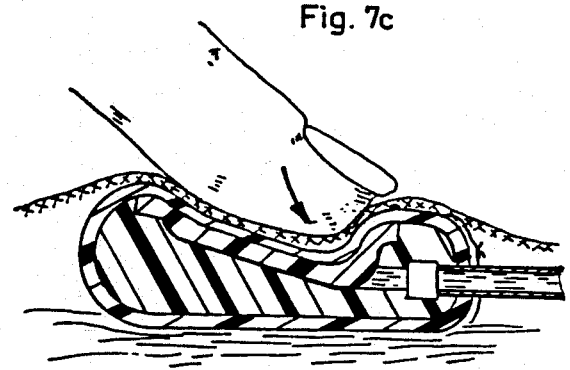

As shown by FIGS. 7a, 7b and 7c, the described device is fully implantable in a subcutaneous zone. Its shape allows easy slippage between the cutaneous line L and the internal musculo-aponeurotic tissues M in a subcutaneous pouch fashioned in the course of implantation. Two sutures S pass through the apertures 9 of the device, thereby fixing it in place, and eliminate the danger of twisting the catheter 7 where it exits from the case.

The injection chamber bounded by the recess 2 and the membrane 4 when at rest may be filled with liquid by injecting it through the skin, the membrane and its coat. This injection may be implemented so as to have available a dose equal to the capacity of said chamber; it is possible too to pierce through with a perfusion needle in a stable manner in order to achieve extended perfusion of a liquid at a suitable pressure. Be it noted that the needle may be made to pierce through tangentially as schematically indicated in FIG. 7b; this is important in perfusion and this feature is absent both from the dome devices (because of the danger of piercing the dome through and through) and from the devices with cylindrical chambers (because of the elevational shape of the chamber). This represents an essential advantage in perfusions requiring extended and stable emplacement of the needle while preserving the patient's freedom of motion: the tangential arrangement of the needle makes it possible to apply the external system S (syringe, pump . . .) at the skin and to easily fix it in place.

The devices remains perfectly impermeable after a very large number of perforations (several thousands); this impermeability is improved over the flexible-dome device on two basic grounds. In the first place, the elastic material of a dome having been perforated many times at close proximity tends to centrifugally deform at the edges of the holes, whereby micro-infiltrations take place in those zones where the holes are close to each other; in the device of the invention however the membrane 4, which is plane at rest, is unaffected by that phenomenon. Further, the double wall formed by the membrane 4 and the flexible coat 8 causes overlaps of material at the perforations so that with the thickness kept constant, these overlaps provide substantially improved impermeability.

As regards injecting an embolus, the operator presses his forefinger onto the membrane until he can feel the hard bottom of the case as shown in FIG. 7c; at that time all of the dose has been expelled into the catheter, and therefore highly accurate injections are made possible.

Because the device is structurally simple and the case 1 is easily manufactured by molding, the production costs for the device of the invention are lowered with respect to the known ones. Also its biocompatibility is outstanding on account of the type of materials being used and the presence of the outer coat 8 (the purpose of this coat being on one hand to improve the biocompatibility and on the other to increase the impermeability after a large number of perforations). The device is free of any kind of metal element and the patient may undergo modern imaging techniques for purposes of exploration without there being interferences or artifacts.

Figure 8:
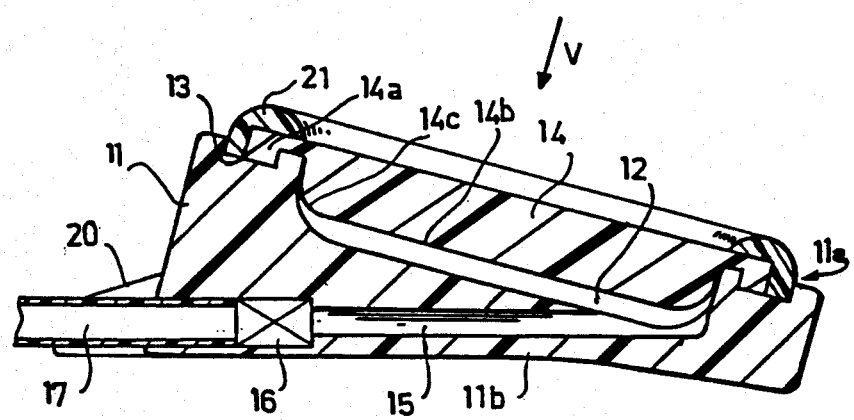
FIGS. 8 and 9 are views of another embodiment mode respectively in section through a plane of symmetry BB' and a topview along the arrow V.
Figure 9:
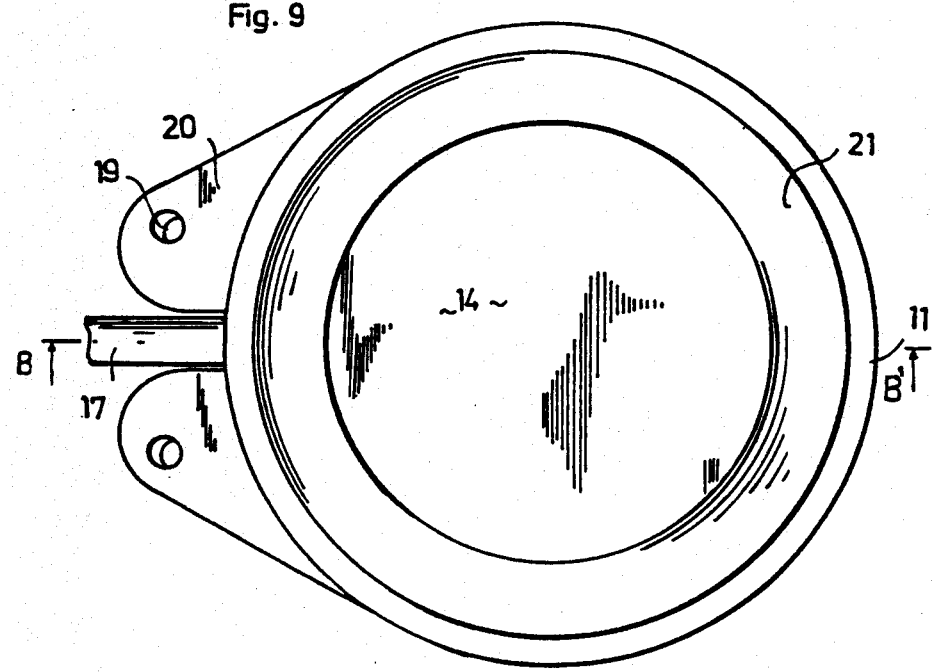

FIGS. 8 and 9 show a variation on scale three times actual size; the differences of this variation relative to the above device are discussed below.

This device includes a molded integral rigid case 11 similar to case 1. However, when seen in topview, this case is circular and includes on its thicker side two small extensions such as 20 with suture holes 19.

As before, the upper side 11a of the case slants relative to the opposite side 11b, whereby the case thickness is decreasing (on the thinner side, the side 11b has an inclined part to retain adequate thickness).

The case 11 includes a recess 12 of which the bottom is parallel to the upper side in its central part and joins this side by a rounded concave peripheral part.

Around the recess 12 the case has a rim 13 with a groove along its entire periphery.

An elastic silicone membrane 14 with a preformed rim 14a is bonded to the rim 13 with a guard ring 21 glued above the assembly The membrane 14 is thicker than the previous one. At rest, its upper side is plane while its lower side is plane over most of its large area 14b and is joined to the performed rim 14a by a rounded convex zone 14c. The membrane 14 deforms to hug the bottom of the recess 12 when being pushed back by the operator's finger.

In this example, the recess 12 has a volume approximately from 0.2 to 0.8 cm$^3$.

Also, the case includes in its thickness a duct 15 passing underneath the recess 12 and issuing into its bottom on the thinner side of the body.

As before, the duct 15 is provided with a bacteria filter 16 and the end of a catheter 17 is bonded into this filter. The case 11 and its membrane may be wholly covered by a flexible silicone coat (omitted).

I claim:

1. A device for subcutaneous implantation in an accessible zone for forming a site for perfusion or chronic injection of a liquid comprising
    a unitary body having a thickness less than its width and breadth and having an upper, active face and a lower face profiled so as to permit said body to slide into said zone,
    said body having a rounded concave recess therewith with a continuous concave bottom and being open at upper face and having a depth less than the width and breadth of said recess at said upper face,
    duct means extending through said body from the bottom of said recess to the outside of said body on one side of said body,
    flexible catheter means secured to said duct means so as to extend said duct outside of said body,
    said body having a peripheral rim around said recess and a substantially planar flexible membrane sealingly secured to said rim and closing said recess, said membrane being self-sealing whereby said membrane may be pierced by a needle for filling said recess and said membrane may be deformed by pressure so as to substantially conform to the shape of said recess for expelling liquid therefrom;
    said body being tapered toward said catheter means and said membrane being positioned on said body in an inclined position with respect to said lower face said recess bottom being angled downwardly toward the duct means, and 2. A device as in claim 1 and wherein said body and said membrane are entirely covered by a flexible coat (8) made of a biocompatible material.

3. A device as in claim 1 and including an antibacterial filter (6) in said duct (5, 15) of said body directly upstream of the end of said catheter means (7, 17).

4. A device as in claim 1 and wherein said upper face (1a, 11a) of the body, and the membrane (4, 14), slope relative to the opposite side of said body (1b, 11b) whereby said body decreases in thickness toward said duct (5, 15) in the recess (2, 12), said duct passing through said case so that the catheter issues from the case in a direction approximately parallel to the plane of one of said faces (1b, 11b).

5. A device as in claim 1 and wherein said recess (2, 12) has a shape which is symmetrical about a longitudinal plane, the bottom of sid recess sloping longitudinally toward said duct (5, 15).

6. A device as in claim 1 and wherein said body (1, 11) comprises a biocompatible rigid plastic.

7. A device as in claim 1 and wherein said membrane (4, 14) conform to the shape of the rim (3, 13) of the recess from an elastic biocompatible plastic of the self-sealing type.

8. A device as in claim 1 and, wherein the recess (2, 12) has a volume between 0.2 and 1.7 $cm^3$ in order to form together with the membrane a chamber with a capacity of a dose of therapeutant.

9. A device as in claim 1 and wherein said body includes on either side of the catheter end (7, 17) two suture holes (9, 19) passing through said body in the direction of its thickness.

* * * * *

UNITED STATES PATENT AND TRADEMARK OFFICE
CERTIFICATE OF CORRECTION

PATENT NO. : 4,710,167
DATED : December 1, 1987
INVENTOR(S) : Guy Lazorthes It is certified that error appears in the above-identified patent and that said Letters Patent is hereby corrected as shown below:

Column 6, after line 68, insert the following:

--said body being provided in the vicinity of said catheter with at least one suture opening.--

Column 8, line 2, after "plastic" insert --member--

Column 8, line 2, change "conform" to --conforms--.

Signed and Sealed this

Seventeenth Day of April, 1990

Attest:

HARRY F. MANBECK, JR.

*Attesting Officer*    *Commissioner of Patents and Trademarks*